(12) United States Patent
Koch et al.

(10) Patent No.: US 11,051,700 B2
(45) Date of Patent: Jul. 6, 2021

(54) BODY CORE TEMPERATURE SENSOR

(71) Applicant: Drägerwerk AG & Co. KGaA, Lübeck (DE)

(72) Inventors: Jochim Koch, Ratzeburg (DE); Thomas Grassl, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 850 days.

(21) Appl. No.: 14/782,105

(22) PCT Filed: Mar. 14, 2014

(86) PCT No.: PCT/EP2014/000703
§ 371 (c)(1),
(2) Date: Oct. 2, 2015

(87) PCT Pub. No.: WO2014/161634
PCT Pub. Date: Oct. 9, 2014

(65) Prior Publication Data
US 2016/0058298 A1 Mar. 3, 2016

(30) Foreign Application Priority Data

Apr. 5, 2013 (DE) .................. 10 2013 005 900.3

(51) Int. Cl.
*A61B 5/01* (2006.01)
*G01K 1/16* (2006.01)
*G01K 13/20* (2021.01)
*A61B 5/00* (2006.01)

(52) U.S. Cl.
CPC ............. *A61B 5/01* (2013.01); *A61B 5/6801* (2013.01); *A61B 5/7278* (2013.01); *G01K 1/165* (2013.01);
(Continued)

(58) Field of Classification Search
CPC .................................. A61B 5/01; G01K 1/165
See application file for complete search history.

(56) References Cited

U.S. PATENT DOCUMENTS 4,539,994 A * 9/1985 Baumbach ......... A61B 5/14542
204/403.06
7,479,116 B2 * 1/2009 Yarden ..................... A61B 5/01
374/E1.011
(Continued)

FOREIGN PATENT DOCUMENTS

CN 101247756 A 8/2008
CN 101548164 A 9/2009
(Continued)

OTHER PUBLICATIONS

Yamakage Michiaki et al.: "Deep temperature monitoring using a zero-heat-flow method". Journal of Anesthesia, Japan Society of Anesthesiology, Tokyo, JP, vol. 17, No. 2, May 1, 2003 (May 1, 2003), pp. 108-115XP002590941, ISSN: 0913-8668 figure 5A.

*Primary Examiner* — Daniel L Cerioni
*Assistant Examiner* — Yasmeen S Warsi
(74) *Attorney, Agent, or Firm* — McGlew and Tuttle, P.C.

(57) ABSTRACT

A double temperature sensor determines the body core temperature of a living being. The double temperature sensor includes a sensor block (2), which on one side carries a first temperature sensor (4) provided for placing on the skin surface and on the other side carries a second temperature sensor (5) spaced from the first. An evaluating unit calculates the body core temperature using the measured values of the first and second temperature sensors. The sensor block (2) is held in a hood-shaped housing shell (1) which is shaped in such a manner that the first temperature sensor (4) on the sensor block and the peripheral outer edge (8) of the housing shell (1) spaced therefrom lie in one plane. When the housing shell (1) is lying on the skin surface, the (Continued)

sensor block (2) is surrounded by an air-filled cavity closed off by the housing shell.

20 Claims, 2 Drawing Sheets

(52) U.S. Cl.
 CPC ...... *G01K 13/20* (2021.01); *A61B 2560/0406* (2013.01); *A61B 2562/04* (2013.01)

(56) References Cited

U.S. PATENT DOCUMENTS

| | | | |
|---|---|---|---|
| 9,101,271 | B2 | 8/2015 | Sattler |
| 2009/0296773 | A1 | 12/2009 | Sattler |
| 2010/0042006 | A1* | 2/2010 | Phua .................. A61B 5/02438 600/500 |
| 2010/0121217 | A1* | 5/2010 | Padiy .................. G01K 13/002 600/549 |
| 2010/0292605 | A1* | 11/2010 | Grassl ...................... G01K 1/16 600/549 |

FOREIGN PATENT DOCUMENTS

| | | |
|---|---|---|
| CN | 101568814 A | 10/2009 |
| CN | 103027666 A | 4/2013 |
| DE | 10 2005 004 933 B3 | 8/2006 |
| DE | 10 2008 026 642 B4 | 6/2010 |
| EP | 2 251 660 A1 | 11/2010 |
| EP | 2387705 B1 | 12/2016 |
| WO | 2005/112547 A2 | 12/2005 |
| WO | 2008078271 A1 | 7/2008 |

* cited by examiner

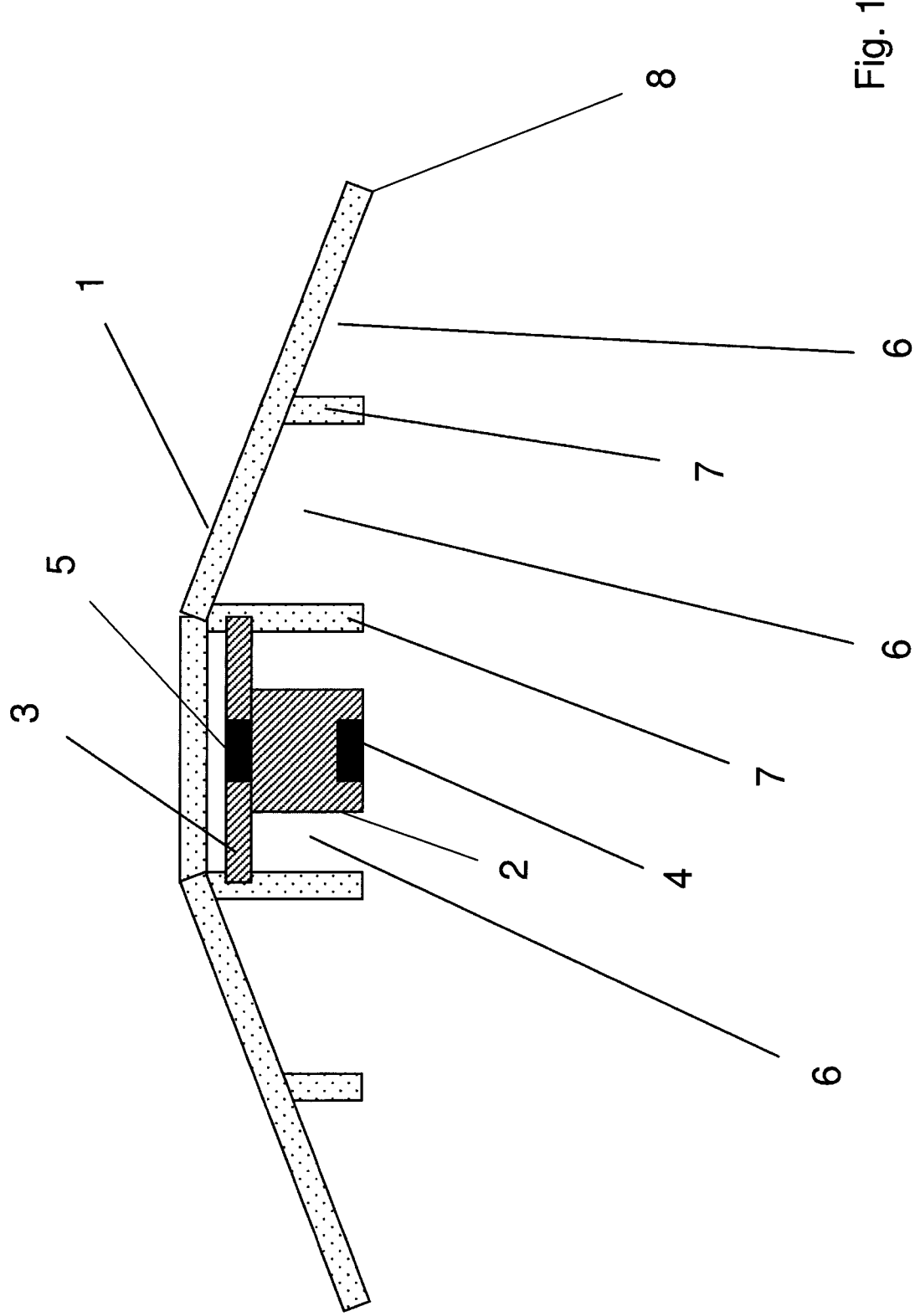

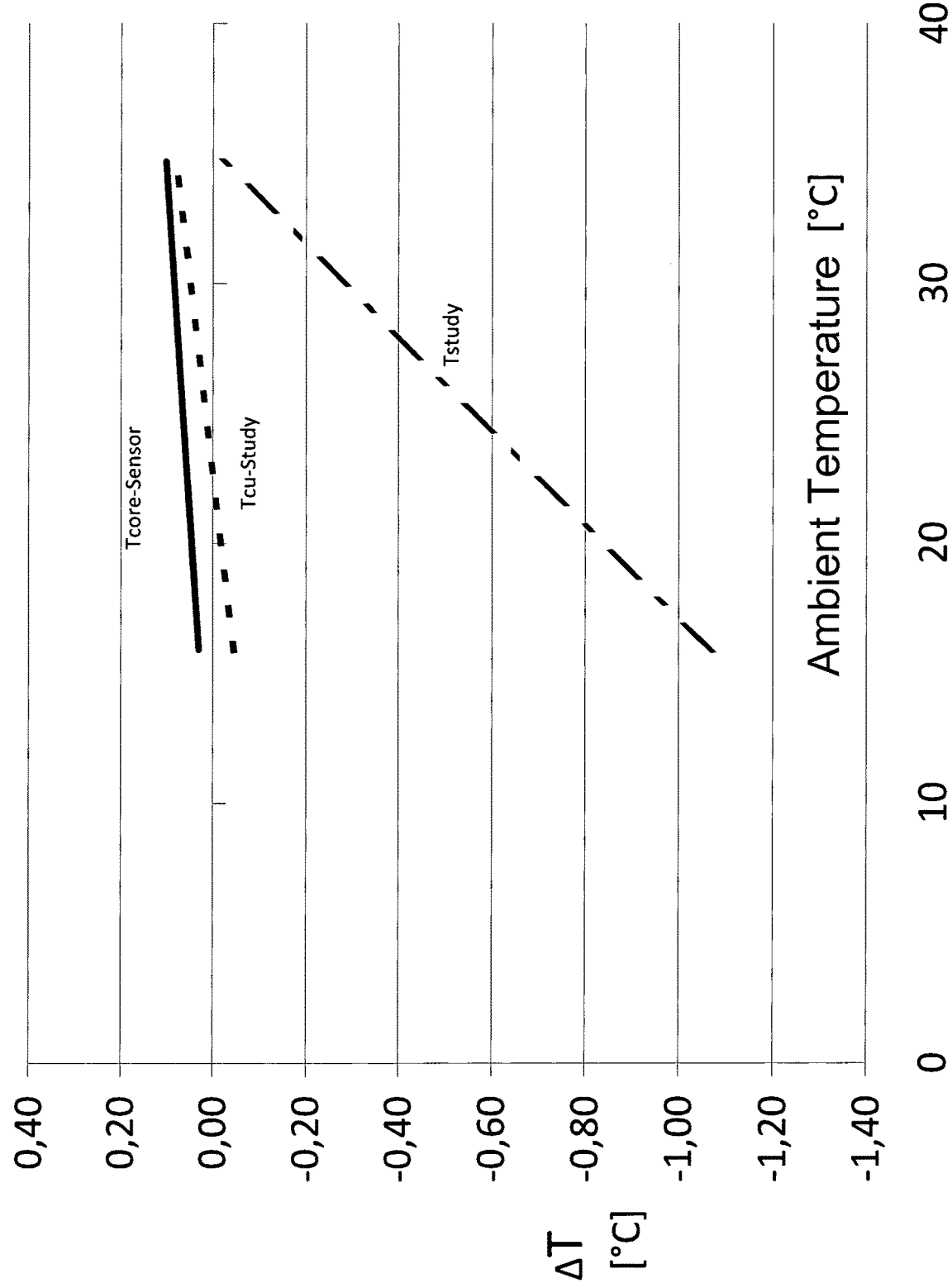

BODY CORE TEMPERATURE SENSOR

CROSS REFERENCE TO RELATED APPLICATIONS

This application is a United States National Phase Application of International Application PCT/EP2014/000703 filed Mar. 14, 2014 and claims the benefit of priority under 35 U.S.C. § 119 of German Patent Application 10 2013 005 900.3 filed Apr. 5, 2013, the entire contents of which are incorporated herein by reference.

FIELD OF THE INVENTION

The present invention pertains to a dual temperature sensor for determining the body core temperature of a living being with a sensor block, which carries a first temperature sensor intended for being placed on the skin surface on one side and a second temperature sensor located at a spaced location from the first one on the other side, and with an analysis unit, which is set up to calculate the body core temperature using the measured values of the first and second temperature sensors.

BACKGROUND OF THE INVENTION

Such a dual temperature sensor measures the temperature on the skin surface with the first temperature sensor and the temperature at the other end of the sensor block at a distance from the first temperature sensor with the second temperature sensor. The heat flow through the material body of the sensor block is obtained from the difference of the temperatures of the first and second sensors, and the body core temperature in the interior of the body of the living being can be calculated from this if the thermal conductivities of the sensor block and the body tissue as well as the skin temperature are known. One problem that compromises the accuracy of the measurement is that heat flows through the sensor block not only in the longitudinal direction, i.e., in the direction connecting the first and second temperature sensors, but also transversely thereto to the side walls of the sensor block. This heat flow taking place transversely is lost for the heat flow to be actually determined by the first and second temperature sensors. Attempts have therefore already been made to reduce this disturbing heat flow taking place transversely in the sensor block or to compensate it in another manner.

DE 10 2005 004 933 B3 describes such a dual temperature sensor. Provisions are made in the dual temperature sensor being described there for the heat flow due to energy loss directed transversely to be compensated by calculation in the sensor block. A third temperature sensor is provided for this purpose on a side surface of the sensor block in order to detect an indicator for the transversely directed heat flow due to energy loss. This temperature of the third temperature sensor will then be included in an expanded formula presented in said patent specification for calculating the core temperature in order to thus calculate the actual body core temperature taking the heat flow due to energy loss into account. However, such a compensation by calculation of the transversely directed heat flow due to energy loss is only an approximate correction, and requires, furthermore, a more expensive apparatus in connection with the third temperature sensor. One should naturally rather seek to eliminate the need for such a correction by calculation in a dual temperature sensor.

The problem of the transversely directed heat flow due to energy loss through the sensor block is tackled in the following manner in the dual temperature sensor known from DE 10 2008 026 642 B4. The dual temperature sensor has a mounting element with an insulator block, into which the first and second temperature sensors are inserted, the first temperature sensor being arranged for detecting a skin-side temperature and the second temperature sensor for detecting an ambient temperature on the upper side. The mounting structure or the insulation block in the material structure shall be designed in this case such that there is an anisotropic heat conduction, especially, of course, an anisotropy such that the heat conduction in the longitudinal direction from the first to the second temperature sensor is greater than the heat conduction in the transverse direction. The transversely directed heat flow due to energy loss, which interferes with the measurement, shall be suppressed in this manner against the heat flow needed for the measurement in the longitudinal direction. Provisions may be made for this for imperfections to be present in the insulation block in the transverse direction for the heat conduction in the form of longitudinally extending holes or concentric groove circle segments. However, only a certain reduction of the transversely directed heat flow due to energy loss, which interferes with the measurement, but no marked reduction of the error of measurement is achieved thereby.

A dual temperature sensor, which likewise has a sensor block with a first temperature sensor and with a second temperature sensor, as in the above-described dual temperature sensors, is known from EP 2 251 660 A1. The sensor block is pressed in this case with a holding clamp onto the skin surface, and the arms of the holding clamp reaching the skin surface are stuck there on the skin with adhesive elements. Furthermore, a spring acts between the holding clamp and the top side of the sensor block facing away from the skin in order to press on the sensor block. To reduce the transversely directed heat flow due to energy loss, the sensor block is surrounded in this case by a foam body as an insulator on all sides. However, heat exchange does still take place through this foam body, so that heat flows due to energy loss still continue to interfere with the measurement. The porous foam of the insulator has an average thermal conductivity of 0.06 W/m o K in such a prior-art dual temperature sensor. The mean diameter of the entire prior-art sensor equals approx. 55 mm, while the sensor block has a diameter of about 10 mm. The average distance between the lateral outer wall of the sensor block and the outer space of the sensor outside the foam material is approx. 22.5 mm. A coefficient of heat transmission of about 2.67 $W/m^2 \cdot K$ is thus calculated. However, the transversely directed heat flow due to energy loss is still present to such an extent that it considerably interferes with the measurement by the dual temperature sensor.

SUMMARY OF THE INVENTION

An object of the present invention is to design a dual temperature sensor such that the effect of transversely directed heat flows due to energy loss through the sensor block becomes negligibly small even without compensation by calculation.

According to the present invention, the sensor block is held in a hood-shaped housing shell, which is shaped such that the first temperature sensor intended to come into contact with the skin surface and the outer edge of the housing shell, which edge extends peripherally at a spaced location therefrom, lie in one plane, so that the sensor block is surrounded by an air-filled cavity closed off by the housing shell when the housing shell is lying on the skin surface. The sensor block is preferably held centrally in the hood-shaped housing shell. It was found that a housing shell, which surrounds the sensor block in a hemisphere and is in contact with the skin surface with its outer peripheral edge at a spaced location from the sensor block, creates an insulating, air-filled cavity, which reduces an interfering, transversely directed heat flow in the sensor block far better than do all prior-art housing structures for dual temperature sensors, so that the error of measurement still caused thereby is absolutely negligible. It will be shown below in connection with the exemplary embodiment that the coefficient of heat transmission is reduced by a factor of more than 2 in a dual temperature sensor according to the present invention compared to a dual temperature sensor whose sensor block is insulated by a surrounding foam. The residual error of measurement that is still left thereafter due to transversely directed heat flow directed laterally from the sensor block is negligible, so that it is also no longer necessary to perform any corrections by calculation.

"Hood-shaped" is defined herein as a housing shell that arches over its interior space over the skin surface within the outer edges like a dome or bell when its outer edges are placed on the skin. However, this hood shape in the sense of the present invention shall not imply a rotation symmetry (like a calotte shell), nor a continuously smooth course of the walls of the housing shell. The housing shell could also have a polygonal outer edge and be composed of pieces with flat wall surfaces, i.e., e.g., in the form of a pyramid or a truncated pyramid. Mixed forms of a truncated cone are likewise possible.

At least one web projecting from the inner wall of the housing shell is formed in the interior of the housing shell in an advantageous embodiment in order to reinforce the housing shell. The housing shell may be made of a plastic with a small wall thickness. To impart sufficient rigidity to the structure, one or more webs formed on the inner wall, which act as reinforcing ribs, may then be present.

In an advantageous embodiment, the height of the web or webs is selected to be such that the edges of the webs facing away from the inner wall of the housing shell lie in the plane of the outer peripheral edge of the housing shell. The subjacent edges of the webs thus likewise lie on the skin surface when the housing shell is in contact with the skin surface, which contributes to the stabilization of the position of the dual temperature sensor in contact with the skin. Further, the lower edges of the webs, just like the outer peripheral edge of the housing shell, may be provided with adhesive elements, so that the dual temperature sensor can thus be held adheringly on the skin surface. It is also possible, in principle, that one or more such webs form a continuous wall in the interior of the housing shell, so that the inner cavity of the housing shell is divided into partial volumes.

The housing shell may have, e.g., a circular outer edge, which lies on the skin surface during use. The housing shell may in this case have, e.g., the shape of a spherical segment (calotte shell). However, the shape of the housing shell, with which the outer edge lies on the skin surface, may be a polygonal circumference or a circumference of another shape. The shape of the outer peripheral edge need not be circular—need not be based on a spherical housing shell. In any case, a mean diameter (or a mean dimension) can be defined for the outer peripheral edge of the housing shell. In an advantageous embodiment, the mean diameter (or the mean dimension) of the peripheral outer edge of the housing shell is more than twice the mean diameter (or the mean dimension) of the sensor block, and the center of the mean diameter (or the mean dimension) of the sensor block is formed by the longitudinal axis, which extends between the first temperature sensor and the second temperature sensor. Even more preferably, the mean diameter (or the mean dimension) of the peripheral outer edge of the housing shell is more than three times the mean diameter (or the mean dimension) of the sensor block. In an especially preferred embodiment, the mean diameter (or the mean dimension) of the outer edge of the housing shell is more than four times the diameter (or the dimension) of the sensor block. In an even more preferred embodiment, the mean diameter (or the mean dimension) of the peripheral outer edge of the housing shell is more than five times the diameter (or the dimension) of the sensor block. The diameter (or the dimension) of the sensor block may equal, for example, about 10 mm, and the diameter (or the dimension) of the peripheral outer edge of the housing shell may equal 55 mm or more. Such a temperature sensor is, on the one hand, easy to handle because of its size, and, on the other hand, the air-filled cavity surrounding the sensor block on the side has a great extension.

In a preferred embodiment, the sensor block is held in the housing shell by at least one fastening element, which is connected, on the one hand, to the sensor block on the side of the second temperature sensor and, on the other hand, is connected directly or indirectly to the inner wall of the housing shell in the central area of the latter. As a result, the heat flow caused by the fastening of the sensor block through the fastening element is not critical, because the heat flow to the second temperature sensor is not practically affected thereby. Two or more thin carriers, which are connected in the central area of the housing shell to the inner wall of said housing shell or to one or more of the webs, may be formed, for example, at the upper end of the sensor block facing away from the skin Such a suspension of the sensor block in the housing shell minimizes any interfering heat flow through the suspension elements.

Another critical point concerning interfering heat flows is linked with the electric line, which connects the first temperature sensor on the skin surface to the analysis unit. Since materials having good electrical conductivity also have, as a rule, good thermal conductivity, there is a problem in that the line leading to the first temperature sensor, which also reaches into the outer space of the housing shall and the analysis unit, brings about an interfering heat flow from the first temperature sensor, because the temperature outside the housing shell is usually lower than the temperature of the skin surface, so that heat can flow off from the first temperature sensor. To circumvent this problem, the line connected to the first temperature sensor is led in the housing shell such that it is in heat-conducting contact with the skin surface during the operation when the housing shell is in contact with the skin surface. Over this path, in heat-conducting contact within the housing shell, the line has an at least partially non-straight or curved course from the first temperature sensor to the outside to the outer peripheral edge of the housing shell, at which the electric line is led out of the housing shell. Consequently, the line is not led directly in the radial direction to the outside to the outer edge of the housing shell and is not led out of the outer edge of the housing shell there, but the line has an at least partially curved or zigzag-like course, so that the length of the line, which is in heat-conducting contact with the skin surface, is increased compared to a direct lead-out from the housing shell. Such a large buffer section is created by this increased line length, which is in heat-conducting contact with the skin surface and is located between the lead-out of the line from the housing shell and the first temperature sensor, that no noticeable heat flow develops at the first temperature sensor within typical measurement times. A heat flow, which takes place through the line, which connects the first temperature sensor to the analysis unit, can be minimized in this way.

The electric line originating from the first temperature sensor may have, for example, at first a radial course up to the vicinity of the outer peripheral edge of the housing shell for this purpose. The line may be led, for example, in the course at a lower edge of a web. Following this, the line may extend peripherally at the outer edge in the interior of the housing shell, in which case it may be led at the peripheral outer edge, extending, for example, over 180°, i.e., over half the peripheral outer edge, before it is led out of the housing shell. It can be achieved in this way that there will be a sufficient electric line length in heat-conducting contact with the skin surface, so that temperature variations will have no noticeable effect on the measurement. As an alternative, a short line may also be led directly to the sensor if the cable consists, for example, of nickel, which has a low electric resistance but low heat conduction.

The present invention will be explained below on the basis of an exemplary embodiment shown in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

BRIEF DESCRIPTION OF THE DRAWINGS

In the drawings:

FIG. 1 is a schematic sectional side view of a dual temperature sensor; and

FIG. 2 is a graph showing an error of measurement caused by transversely directed heat flow as a temperature difference between the measured core temperature and the actual core temperature of the body as a function of the ambient temperature for the dual temperature sensor according to the present invention compared to conventional dual temperature sensors.

DESCRIPTION OF THE PREFERRED EMBODIMENTS

The dual temperature sensor shown in FIG. 1 has a sensor block 2, which carries a first temperature sensor 4 on a side facing the skin surface and a second temperature sensor 5 at the opposite end facing away from the skin. The sensor block 2 is shielded in a hemisphere by a hood-shaped housing shell 1. The housing shell 1 is shaped such that an outer peripheral edge 8 of the hood-shaped housing shell 1 lies in a same plane as the lower edge surface first temperature sensor 4, so that the housing shell forms a closed, air-filled cavity 6 around the sensor block 2 when the dual temperature sensor is in contact with the skin surface. One or more webs 7, originating from the inner wall of the housing shell, which impart a greater rigidity to the housing shell, may be provided in the interior of the housing shell 1. A height of the webs 7 may be dimensioned such that lower edges of the webs 7 likewise lie in the plane defined by the outer peripheral edge 8 of the housing shell and are thus likewise lying on the skin when the dual temperature sensor is in contact with the skin surface. The outer peripheral edge 8 and the lower edges of the webs 7 may be provided with adhesive elements, so that the dual temperature sensor can be stuck to the skin surface. As an alternative, the dual temperature sensor may be held on the skin surface by a holding strap or in another manner.

The sensor block 2 is held in a center of the housing shell 1 by one or more fastening elements 3, which fastening elements 3 may be designed, for example, as thin brackets. Due to the fastening elements 3 being arranged at the upper outer end of the sensor block 2, the effect of heat flow through the fastening elements on the temperature measurement by the second temperature sensor 5 is minimized, because the heat flow towards the second temperature sensor 5 is no longer affected appreciably thereby.

The mean external diameter of the peripheral outer edge 8 of the housing shell 1 is preferably several times the diameter of the sensor block 2. The mean diameter (or a mean dimension) of the housing shell may equal, for example, 55 mm, while the sensor block has a diameter (a width dimension) of 10 mm.

An air-filled, closed cavity, by which the lateral heat flow due to energy loss in the sensor block 2 is minimized, is thus formed around the sensor block 2. A coefficient of heat transmission of 1.16 $W/m^2 \cdot K$ is obtained for the dual temperature sensor according to the present invention with the above-mentioned dimensions and an average thermal conductivity of the air of 0.026 $W/m^2 \cdot K$. By contrast, as was shown above, a coefficient of heat transmission of 2.67 $W/m^2 \cdot K$, which is more than double that of the dual temperature sensor according to the present invention, is obtained for a conventional dual temperature sensor.

FIG. 2 shows the deviation $\Delta T$ of the measured body core temperature from the actual body core temperature of an artificial head as a function of the ambient temperature, wherein the results of the dual temperature sensor according to the present invention (Tcore-Sensor) are compared to those of a conventional, foam-insulated dual temperature sensor (Tstudy) and those of a dual temperature sensor with correction calculation (Tcu-STUDY), as in DE 10 2005 004 933 B3. It can be seen that only a negligible deviation within 0.1° C. is obtained for the dual temperature sensor according to the present invention, which is comparable to a dual temperature sensor with correction by calculation, as is described in DE 10 2005 004 933 B3. By contrast, the foam-insulated conventional dual temperature sensor shows a considerably greater deviation as a function of the ambient temperature.

Compared to the dual temperature sensor known from DE 10 2008 026 642 B4, the dual temperature sensor according to the present invention does once again lead to an improvement in respect to the suppression of the interfering lateral heat flow from the sensor block. It is claimed in said patent that the lateral heat flow is lower than the heat conduction in the longitudinal direction through the sensor block by a factor of 2 to 20. There is a heat conduction of about KS=28 to 90 $W/m^2 \cdot K$, depending on the design of the sensor block, through the sensor block 2 as is used in the present invention. As was mentioned above, the interfering lateral heat flow is only 1.16 $W/m^2 \cdot K$ for the dual temperature sensor in a shielded air-filled cavity. The suppression of the lateral heat flow is consequently even stronger or, in other words, the anisotropy of the heat conduction is even greater than in case of the structure described in DE 10 2008 026 642 B4. The decisive difference between the dual temperature sensor structure according to the present invention and the dual temperature sensor described in DE 10 2008 026 642 B4 is that the surrounding sensor housing does not consist of a solid material, which is provided with holes or grooves at individual points in order to interfere with the lateral heat conduction, but the housing shell shields the sensor block in a hemisphere or partial enclosure (that cooperates with the skin surface) in the dual temperature sensor according to the present invention and holds the sensor block only on a top side of the sensor block, in the central area of the housing shell in a cavity (the enclosed space) of the housing shell. The sensor block is surrounded and closed by the housing shell 1, which lies on the skin surface with an outer peripheral edge 8 of the housing shell 1, such that the sensor block 2 is laterally surrounded by an air-filled cavity.

While specific embodiments of the invention have been shown and described in detail to illustrate the application of the principles of the invention, it will be understood that the invention may be embodied otherwise without departing from such principles.

The invention claimed is:

1. A dual temperature sensor for determining a body core temperature of a living being, the dual temperature sensor comprising:
   a sensor block, which carries a first temperature sensor comprising a skin contact surface configured to directly contact a skin surface of the living being on one side and the sensor block carries a second temperature sensor at a spaced location from the first temperature sensor on another side;
   a hood-shaped housing shell, the hood-shaped housing shell being open on one side, the sensor block being held in the housing shell, which housing shell is shaped such that the first temperature sensor at the sensor block and an outer peripheral edge of the housing shell, extending peripherally at a spaced location therefrom, are lying in one plane, so that the sensor block is surrounded by a closed, air-filled cavity when the housing shell lies on the skin surface, wherein the one side is configured to be at least partially closed by the skin surface when the housing shell lies on the skin surface, the first temperature sensor being located at a spaced location from the hood-shaped housing shell; and
   at least one fastening element, wherein the sensor block is held in the housing shell by the at least one fastening element, which is connected to the sensor block on the side of the second temperature sensor and is connected to the inner wall of the housing shell in a central area thereof, at least a portion of the second temperature sensor being embedded in the at least one fastening element, the portion of the second temperature sensor comprising a second temperature sensor surface, the second temperature sensor surface being in contact with the at least one fastening element.

2. A dual temperature sensor in accordance with claim 1, wherein the sensor block and the at least one fastening element are located at a spaced location from the hood-shaped housing shell, the first temperature sensor comprising a first temperature sensor outer surface, the sensor block comprising a sensor block skin contact surface configured to directly contact the skin surface of the living being, the first temperature sensor outer surface being located adjacent to the sensor block skin contact surface.

3. A dual temperature sensor in accordance with claim 1, wherein:
   the housing shell further comprises an inner wall; and
   at least one projecting web is formed by the inner wall of the housing shell in an interior of the housing shell in order to reinforce the housing shell.

4. A dual temperature sensor in accordance with claim 3, wherein the at least one web is dimensioned such that an edge of the web, facing away from the inner wall of the housing shell, lies in the plane of the outer peripheral edge of the housing shell.

5. A dual temperature sensor in accordance with claim 1, wherein a mean diameter of the outer peripheral edge of the housing shell is more than twice a mean diameter of the sensor block, wherein a center of the mean diameter of the sensor block is formed by a longitudinal axis that extends between the first and second temperature sensors.

6. A dual temperature sensor in accordance with claim 4, wherein a mean diameter of the outer peripheral edge of the housing shell is more than four times the mean diameter of the sensor block, wherein the center of the mean diameter of the sensor block is formed by the longitudinal axis that extends between the first and second temperature sensors.

7. A dual temperature sensor in accordance with claim 1, further comprising an electric line, wherein the line is connected to the first temperature sensor and is led in the housing shell such that the line is in heat-conducting contact with the skin surface during operation when the peripheral outer edge of the housing shell is in contact with the skin surface during operation, and in this heat-conducting contact within the housing shell, the line has an at least partially non-straight course on a path from the first temperature sensor to outside of the outer peripheral edge of the housing shell, at which outer peripheral edge the line is led out of the housing shell.

8. A dual temperature sensor in accordance with claim 1, further comprising an electric line, wherein the line is connected to the first temperature sensor and extends, starting from the first temperature sensor, radially to the outside to the outer peripheral edge of the housing shell, and, following same, the line is led within the housing shell in the circumferential direction along the peripheral edge up to the point at which the line is led out of the housing shell.

9. A dual temperature sensor in accordance with claim 7, wherein the path length of the line of the first temperature sensor in the interior of the housing shell in heat-conducting contact with the skin surface is 5 cm or longer.

10. A dual temperature sensor for determining a body core temperature of a living being, the dual temperature sensor comprising:
    a sensor block, which carries a first temperature sensor and carries a second temperature sensor at a spaced location from the first temperature sensor on another side wherein the sensor block is configured to directly contact the skin surface of the living being;
    a hood-shaped housing shell comprising an opening on one side of the hood-shaped housing shell, the sensor block being held in the housing shell, which housing shell is shaped such that a skin engaging contact surface of the first temperature sensor at the sensor block and a skin engaging contact surface of an outer peripheral edge of the housing shell, extending peripherally at a spaced location therefrom, are lying in one plane, so that the sensor block is surrounded by a closed, air-filled cavity when the housing shell lies on the skin surface, wherein the opening is configured to be closed via the skin surface when the housing shell lies on the skin surface;
    at least one fastening element, wherein the sensor block is held in the housing shell by the at least one fastening element, which is connected to the sensor block on the side of the second temperature sensor and is connected to an inner wall of the housing shell in a central area thereof, at least a portion of the second temperature sensor being embedded in the at least one fastening element, the portion of the second temperature sensor comprising a second temperature sensor surface, the second temperature sensor surface being in contact with the at least one fastening element.

11. A dual temperature sensor in accordance with claim 10, wherein the first temperature sensor is located at a spaced location from the hood-shaped housing shell, the one plane being a single plane, the skin engaging contact surface of the first temperature sensor and the skin engaging contact surface of the outer peripheral edge of the housing shell being arranged in the single plane.

12. A dual temperature sensor in accordance with claim 11, wherein the sensor block and the fastening element are located at a spaced location from the hood-shaped housing shell.

13. A dual temperature sensor in accordance with claim 10, wherein at least a portion of the first temperature sensor is embedded in the sensor block.

14. A dual temperature sensor in accordance with claim 10, wherein the sensor block comprises a sensor block skin contact surface configured to directly contact the skin surface of the living being, the first temperature sensor comprising a skin contact surface configured to directly contact the skin surface of the living being on one side, at least a portion of the skin contact surface of the first temperature sensor being located adjacent to the sensor block skin contact surface.

15. A dual temperature sensor for determining a body core temperature of a living being, the dual temperature sensor comprising:
a sensor block, which carries a first temperature sensor on one side and carries a second temperature sensor at a spaced location from the first temperature sensor on another side, wherein the sensor block comprises a sensor block skin contact surface configured to directly contact the skin surface of the living being;
a hood-shaped housing shell comprising an opening on one side thereof, the sensor block being held in the housing shell, which housing shell is shaped such that the sensor block skin contact surface and a skin engaging contact surface of an outer peripheral edge of the housing shell, extending peripherally at a spaced location therefrom, are lying in one plane, so that the opening is closed and the sensor block is surrounded by a closed, air-filled cavity when the housing shell lies on the skin surface; and
at least one fastening element, wherein the sensor block is held in the housing shell by the at least one fastening element, which is connected to the sensor block on the side of the second temperature sensor and is connected to an inner wall of the housing shell in a central area thereof, at least a portion of the second temperature sensor being embedded in the at least one fastening element, the portion of the second temperature sensor comprising a second temperature sensor surface, the second temperature sensor surface being in contact with the at least one fastening element.

16. A dual temperature sensor in accordance with claim 15, wherein the first temperature sensor comprises a first temperature sensor skin contact surface configured to directly contact one area of the skin surface of the living being, the sensor block skin contact surface being configured to directly contact another area of the skin surface of the living being, the sensor block skin contact surface being located adjacent to the first temperature sensor skin contact surface, the one plane being a single plane, the sensor block skin contact surface and the skin engaging contact surface of the outer peripheral edge of the housing shell being arranged in the single plane.

17. A dual temperature sensor in accordance with claim 16, wherein the sensor block skin contact surface and the first temperature sensor skin contact surface are provided in the one plane, the sensor block and the at least one fastening element are located at a spaced location from the housing shell.

18. A dual temperature sensor in accordance with claim 15, further comprising a plurality of webs extending from the housing shell, each of the plurality of webs having a web skin contact surface, the at least one fastening element being connected to the plurality of webs, wherein the at least one fastening element is located at a spaced location from the housing shell.

19. A dual temperature sensor in accordance with claim 10, further comprising a plurality of webs extending from the housing shell, each of the plurality of webs having a web skin contact surface, the at least one fastening element being connected to the plurality of webs, wherein the at least one fastening element is located at a spaced location from the housing shell.

20. A dual temperature sensor in accordance with claim 1, further comprising a plurality of webs extending from the housing shell, each of the plurality of webs having a web skin contact surface, the at least one fastening element being connected to the plurality of webs, wherein the at least one fastening element is located at a spaced location from the housing shell.

* * * * *